(12) United States Patent
Yamamoto (10) Patent No.: US 6,689,122 B2
(45) Date of Patent: Feb. 10, 2004

(54) ENDOSCOPIC INSTRUMENT

(75) Inventor: Tetsuya Yamamoto, Hidaka (JP)

(73) Assignee: Olympus Corporation, Tokyo (JP)

( * ) Notice: Subject to any disclaimer, the term of this patent is extended or adjusted under 35 U.S.C. 154(b) by 46 days.

(21) Appl. No.: 09/859,846

(22) Filed: May 17, 2001

(65) Prior Publication Data

US 2001/0047124 A1 Nov. 29, 2001

(30) Foreign Application Priority Data

May 17, 2000 (JP) ........................................ 2000-145528

(51) Int. Cl.$^7$ .............................................. A61B 17/28
(52) U.S. Cl. .......................................... 606/1; 606/205
(58) Field of Search .......................... 606/1, 170, 205, 606/206, 207, 208, 209; 600/104, 105, 106, 127, 128, 129

(56) References Cited

U.S. PATENT DOCUMENTS

| | | | |
|---|---|---|---|
| 3,521,620 A | | 7/1970 | Cook |
| 3,973,556 A | | 8/1976 | Fleischhacker et al. |
| 4,080,706 A | | 3/1978 | Heilman et al. |
| 4,634,042 A | | 1/1987 | Smith |
| 4,721,116 A | * | 1/1988 | Schintgen et al. .......... 600/564 |
| 4,817,630 A | | 4/1989 | Schintgen et al. |
| 4,982,727 A | * | 1/1991 | Sato ............... 600/104 |
| 5,133,727 A | | 7/1992 | Bales et al. |
| 5,228,451 A | | 7/1993 | Bales et al. |
| 5,360,432 A | * | 11/1994 | Shturman ............ 606/159 |
| 5,558,100 A | | 9/1996 | Cox |
| 5,571,129 A | | 11/1996 | Porter |
| 5,591,202 A | * | 1/1997 | Slater et al. ............ 606/170 |
| 5,766,184 A | * | 6/1998 | Matsuno et al. ............ 604/15 |
| 5,810,876 A | * | 9/1998 | Kelleher ............ 606/170 |
| 6,066,102 A | * | 5/2000 | Townsend et al. .......... 600/104 |
| 6,299,630 B1 | * | 10/2001 | Yamamoto ............ 606/170 |
| 6,375,650 B1 | * | 4/2002 | Ouchi ............ 600/139 |

FOREIGN PATENT DOCUMENTS

| | | |
|---|---|---|
| DE | 1 491 851 | 4/1970 |
| DE | 29 26 339 | 1/1980 |
| DE | 44 90 796 T1 | 1/1996 |
| DE | 691 17 028 T2 | 9/1996 |
| DE | 198 15 840 A1 | 10/1998 |
| FR | 2 613 231 | 10/1998 |
| JP | 9-508560 | 9/1997 |
| JP | 9-508561 | 9/1997 |

* cited by examiner

*Primary Examiner*—John Mulcahy
*Assistant Examiner*—Kenneth G. Schopfer
(74) *Attorney, Agent, or Firm*—Scully, Scott, Murphy & Presser (57) ABSTRACT

An endoscopic instrument of the present invention comprises a flexible insert section capable of being passed through a forceps channel of an endoscope, an operating wire located in a bore of the insert section and movable in the axial direction of the insert section, an operating section connected to the proximal end side of the insert section and used to move the operating wire forward and backward, and a treatment section attached to the distal end of the insert section and adapted to be operated as the operating wire is moved forward and backward. The operating wire is composed of at least one wire member, a resin member is located on or adhered to at least a part of the outer surface of the operating wire, at least the inner surface of the insert section is formed of a metallic coil, and a micro-flat portion is provided at least on that surface portion of an element wire of the coil which faces the operating wire.

19 Claims, 15 Drawing Sheets

ENDOSCOPIC INSTRUMENT

CROSS-REFERENCE TO RELATED APPLICATIONS

This application is based upon and claims the benefit of priority from the prior Japanese Patent Application No. 2000-145528, filed May 17, 2000, the entire contents of which are incorporated herein by reference.

BACKGROUND OF THE INVENTION

The present invention relates to an endoscopic instrument capable of being introduced into the human body through a forceps channel of an endoscope and used for medical treatment.

Figure 23:
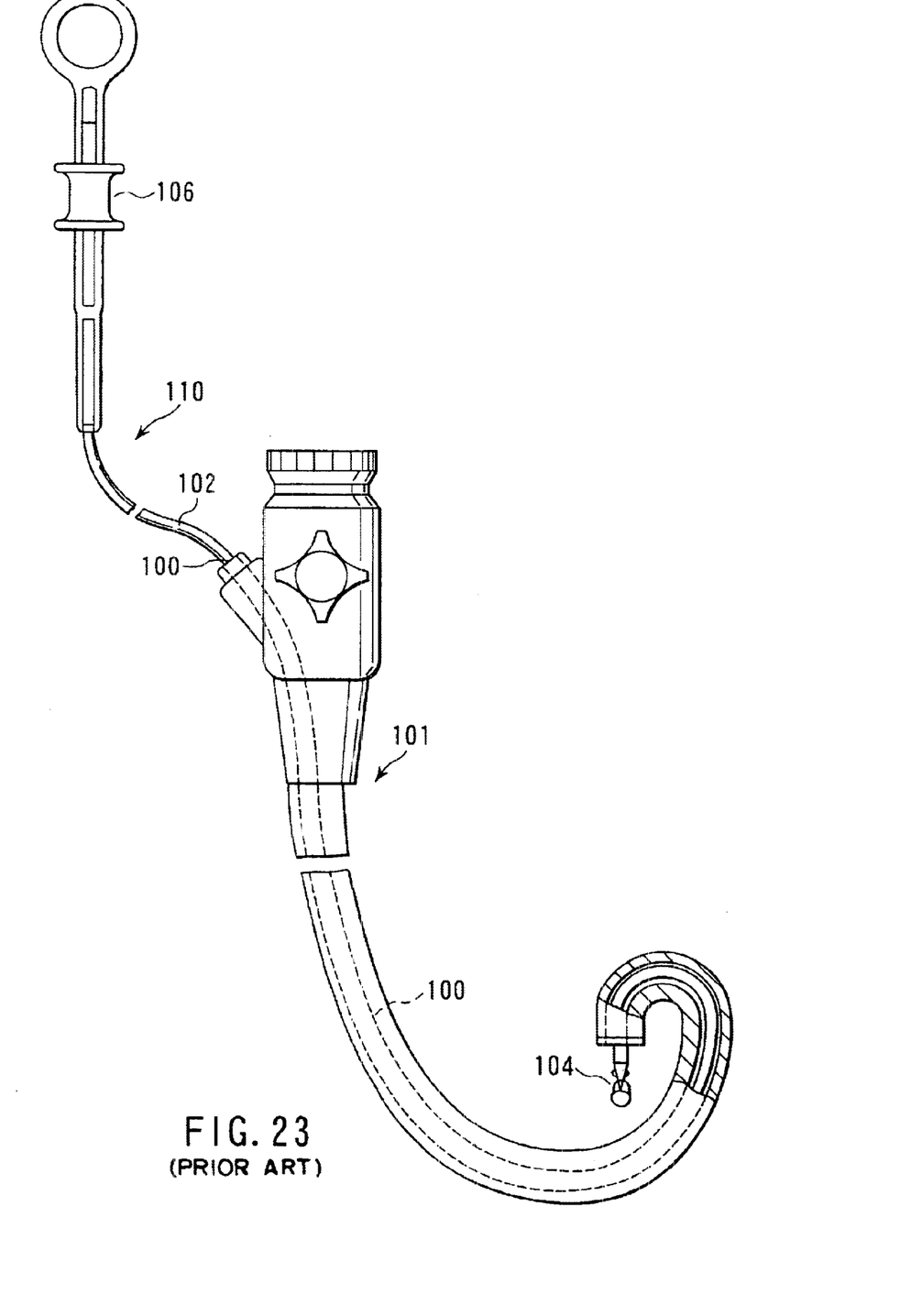
FIG. 23 is a view showing an endoscopic instrument in a general working state.
Figure 24:
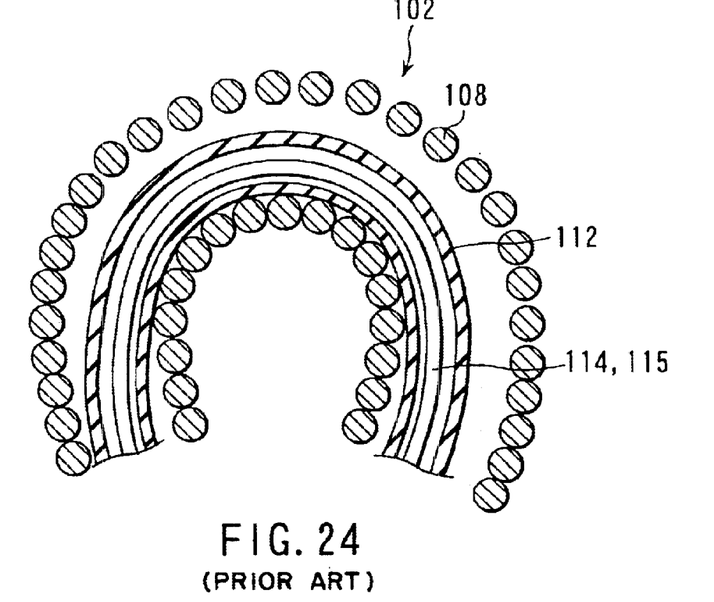
FIG. 24 is a sectional view showing a state of an insert section of the endoscopic instrument in a curved endoscope.

Conventionally, there is an endoscopic instrument 110 that comprises an elongated insert section 102 capable of being passed through a forceps channel 100 of an endoscope 101, a treatment section 104 attached to the distal end of the insert section 102, and an operating section 106 on the proximal end side of the insert section 102, as shown in FIG. 23. A desired treatment is conducted as the distal treatment section 104 is operated by pushing or pulling an operating wire, which is movably passed through the insert section 102, by means of the operating section 106. In the insert section 102 of the endoscopic instrument 110, as shown in FIG. 24, for example, a plastic tube 112 is located in a coil 108 that is formed of an element wire having a circular cross section, and a pair of operating wires 114,115 are passed through the tube 112 (cf. PCT National Publication No. 9-507420 (Symbiosis) or U.S. Pat. No. 5,133,727 (Symbiosis)).

Figure 25:
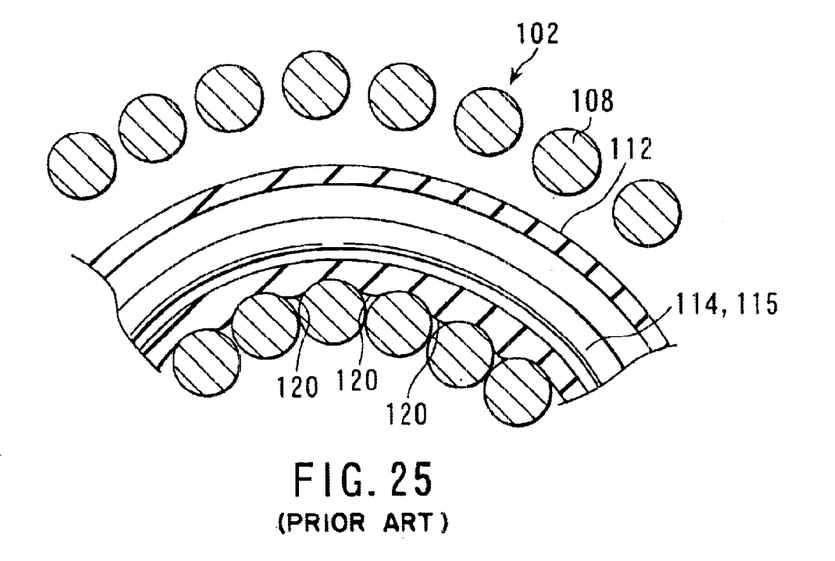
FIG. 25 is an enlarged sectional view showing the state of the insert section of the endoscopic instrument in the curved endoscope.

In some endoscopic instruments such as biopsy forceps in which the distal treatment section 104 requires a force in carrying out treatment, a force of 10 kgf or more may be applied to the operating section 106 on the proximal end side. In this case, a similar force acts on the operating wires 114,115 that are passed through the coil 108 of the insert section 102. In the endoscopic instrument (see FIG. 24) having the construction described in PCT National Publication No. 9-507420 or U.S. Pat. No. 5,133,727, therefore, the force that is directed toward the center of the curvature acts on the operating wires 114, 115 when the operating section 106 is operated with the endoscope 101 curved, as shown in FIG. 23. As shown in FIGS. 24 and 25, moreover, the plastic tube 112, which is designed to smoothen the slide of the wires 114, 115, bites into the grooves 120 between the element wires of the coil 108, so that the force of the operating section 106 cannot be efficiently transmitted to the distal treatment section. In this case, the wires 114, 115 and the tube 112 are not fixed. Since the sliding resistance between the coil 108 and the tube 112 is higher than the resistance between the tube 112 and the wires 114,115, however, the wires 114,115 and the tube 112 move as one body in the coil 108 when the wires 114,115 are slid. If the movement of the plastic tube 112 is prevented, therefore, the force that is transmitted to the operating wires 114,115 attenuates.

BRIEF SUMMARY OF THE INVENTION

The object of the present invention is to provide an endoscopic instrument capable of efficiently transmitting an operating force to a treatment section without being influenced by the curved state of an endoscope.

The above object of the present invention is achieved by the following endoscopic instrument. The endoscopic instrument according to the invention comprises a flexible insert section capable of being passed through a forceps channel of an endoscope, an operating wire located in a bore of the insert section and movable in the axial direction of the insert section, an operating section connected to the proximal end side of the insert section and used to move the operating wire forward and backward, and a treatment section attached to the distal end of the insert section and adapted to be operated as the operating wire is moved forward and backward. The operating wire is composed of at least one wire member, a resin member is located on or adhered to at least a part of the outer surface of the operating wire, at least the inner surface of the insert section is formed of a metallic coil, and a micro-flat portion is provided at least on that surface portion of an element wire of the coil which faces the operating wire.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

An embodiment of the present invention will now be described with reference to the accompanying drawings. Although a biopsy forceps will be described as an example of an endoscopic instrument according to this embodiment, it is to be understood that the invention may be applied to any other instruments such as a grasping forceps, thread cutting forceps, scissor-type forceps, hot-biopsy forceps, high-frequency snare, rotary clip device, ligature device, lithotripter, stone collecting basket, cytological brush, papillotome, etc.

Figure 1:
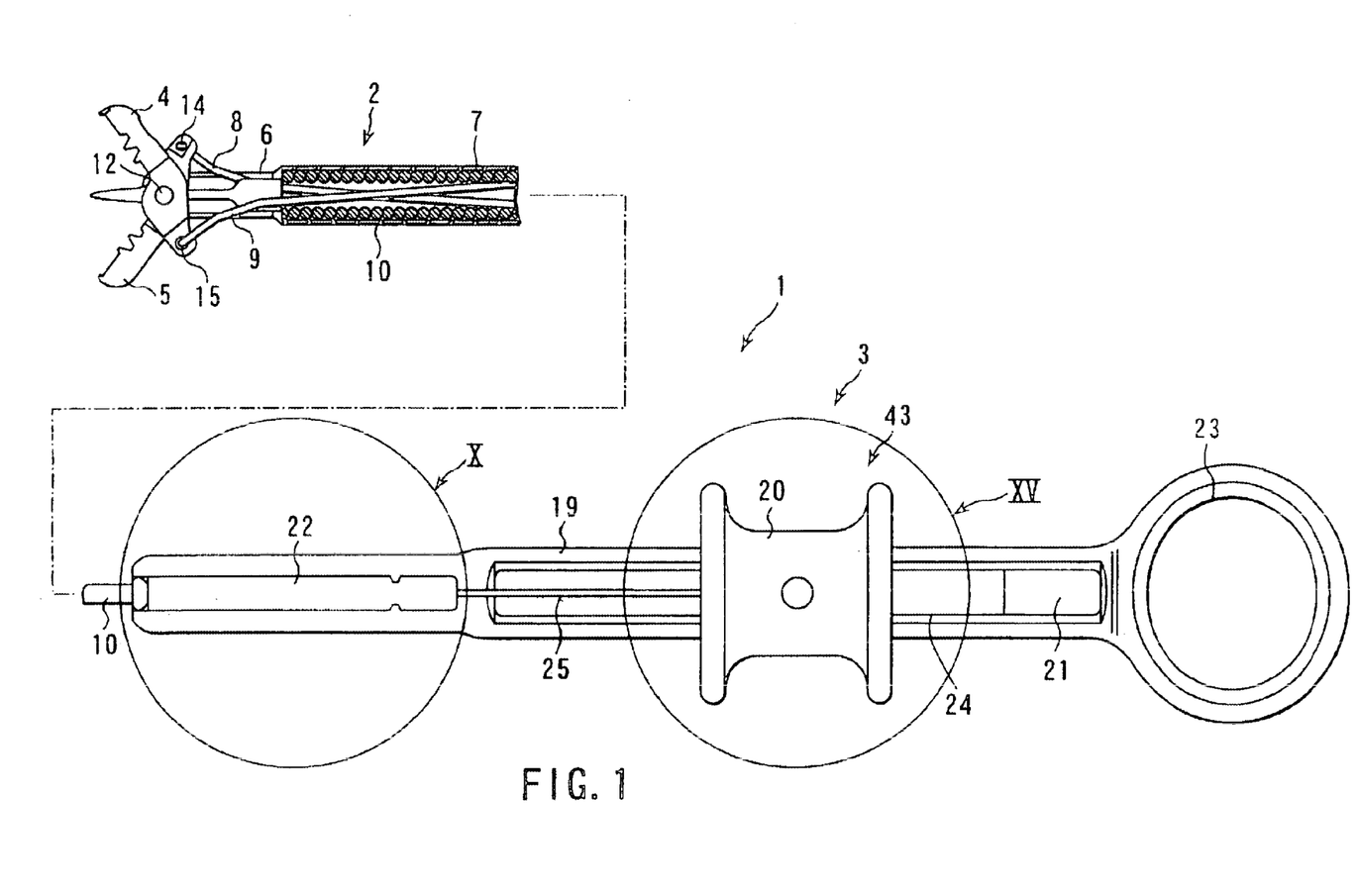
FIG. 1 is a general view of an endoscopic biopsy forceps (endoscopic instrument) according to an embodiment of the present invention.
Figure 2A:
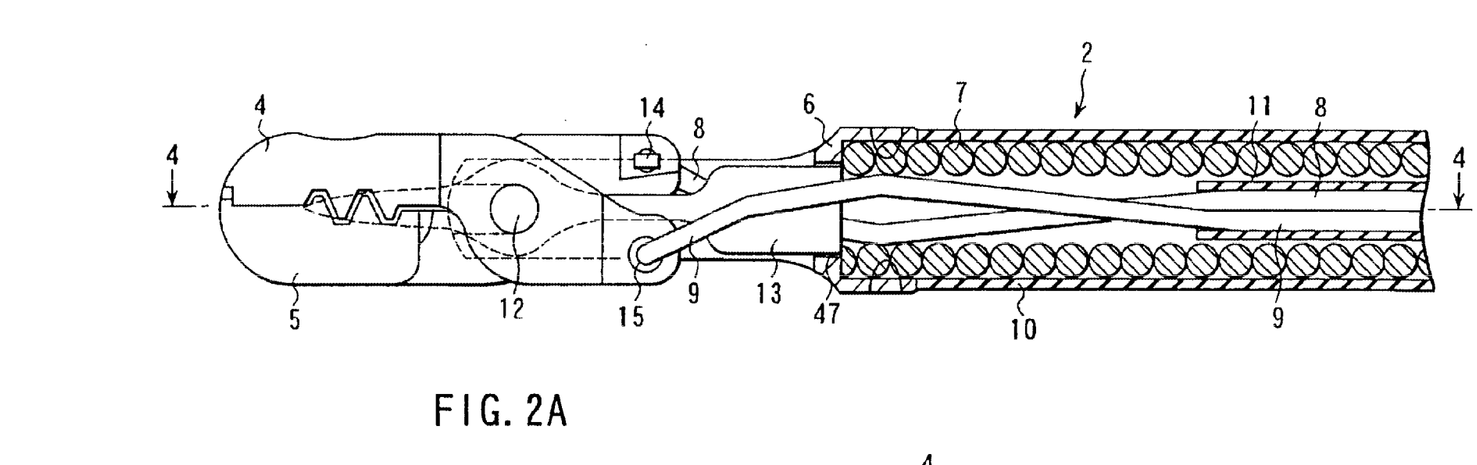
FIG. 2A is a side view, partially in section, showing biopsy cups of the endoscopic biopsy forceps of FIG. 1 in a closed state.
Figure 2B:
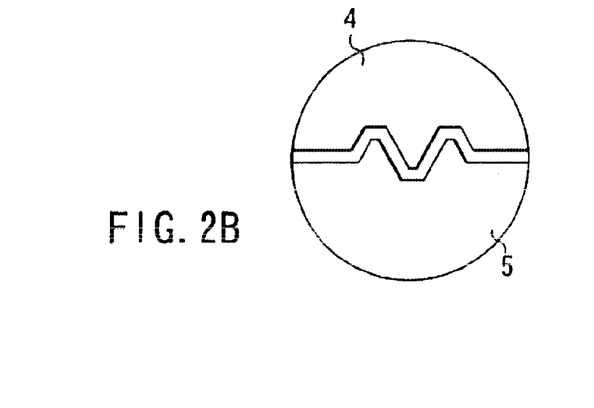
FIG. 2B is an axial front view of the biopsy cups of the biopsy forceps of FIG. 2A.

As shown in FIG. 1, the endoscopic biopsy forceps 1 comprises a flexible insert section 2, which can be passed through a forceps channel of an endoscope, and an operating section 3. As shown in FIGS. 1 to 4, the insert section 2 includes a coil 7 having a bore, an outer tube 10 formed covering the outer surface of the coil 7 by tubing or a heat-shrinkable tube, an inner tube 11 located in the bore of the coil 7, two operating wires 8 and 9 each formed of a solid or stranded wire movable in a bore of the inner tube 11. The insert section 2 further includes a cup holding member 6 fitted on and fixed to the distal end of the coil 7 by laser welding, brazing, soldering, or caulking, a pair of biopsy cups 4 and 5 for use as treatment sections rotatably mounted near the distal end of the cup holding member 6 by means of a pin 12, and a needle 13. The distal end side of the needle 13 is fixed between the biopsy cups 4 and 5 by means of the pin 12, while the proximal side of the needle 13 is fitted in a hole 47 that is formed near the proximal side of the cup holding member 6.

Figure 5:
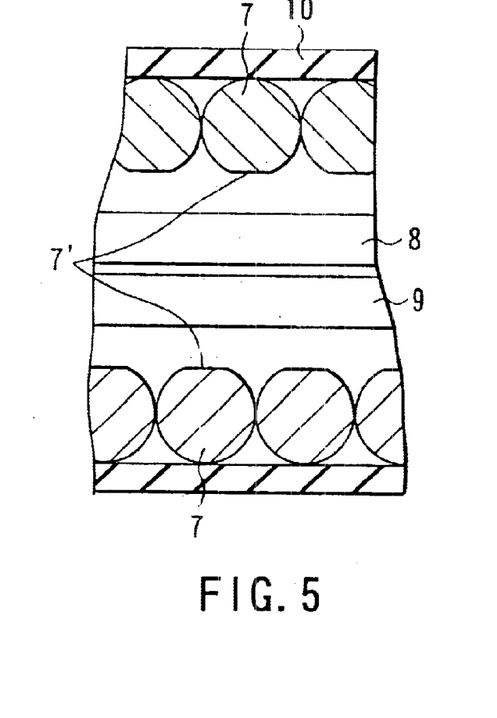
FIG. 5 is an enlarged sectional view showing an example of the profile of a coil.
Figure 6:
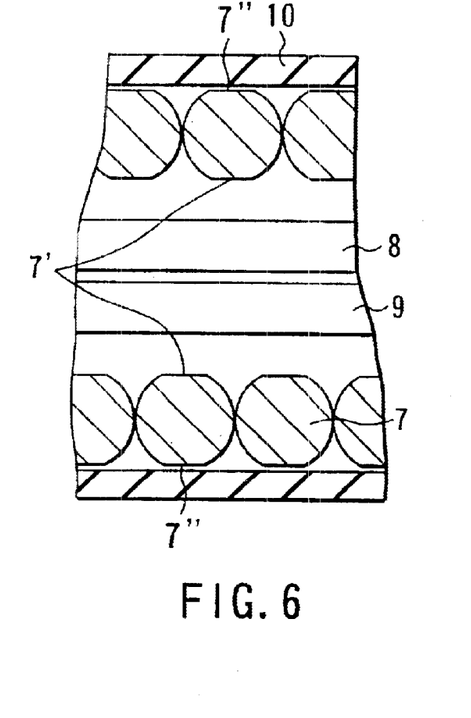
FIG. 6 is an enlarged sectional view showing another example of the profile of a coil.
Figure 7:
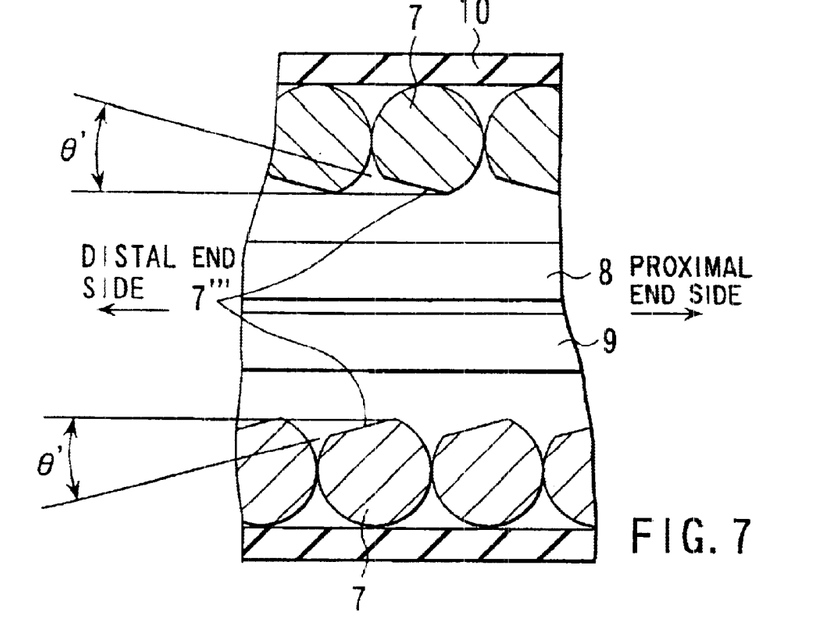
FIG. 7 is an enlarged sectional view showing still another example of the profile of a coil.
Figure 8:
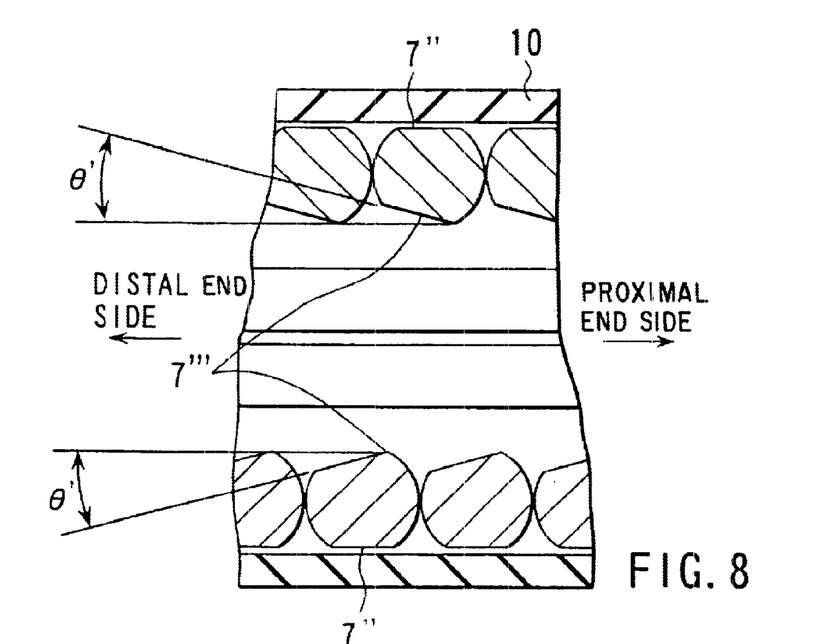
FIG. 8 is an enlarged sectional view showing a further example of the profile of a coil.
Figure 22:
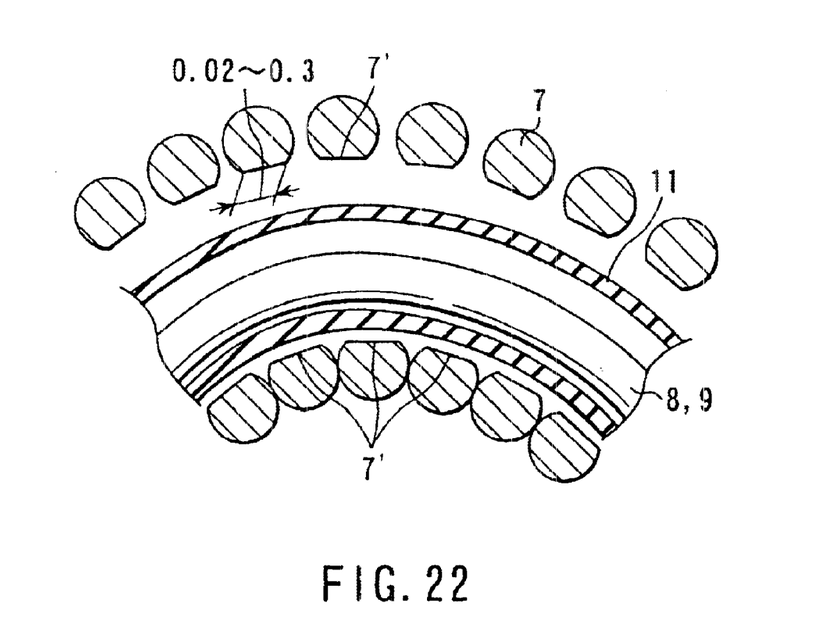
FIG. 22 is a sectional view for illustrating the function of a configuration according to the one embodiment of the invention.

As shown in FIG. 5, an axially extending micro-flat portion 7' is formed on the inner surface of the coil 7, covering its overall length or at least a part thereof. In this case, the length of the micro-flat portion 7' for the cross section of each element wire that extends in the longitudinal direction of the coil 7 is adjusted to 0.02 to 0.3 mm (see FIG. 22) as the coil 7 is viewed along its cross section in the longitudinal direction. As shown in FIG. 6, moreover, an axially extending micro-flat portion 7" may be also formed on the outer surface of the coil 7. In order to further improve the transmissibility of the operating wires 8 and 9 that are pulled to the proximal end side, a micro-flat portion 7'" that is inclined at an angle θ' to the axial direction may be formed on the inner surface of the coil 7 so that the bore of the coil 7 is tapered toward the proximal ens side, as shown in FIGS. 7 or 8. Preferably, in this case, the angle θ' should be adjusted to 45° or more. If the micro-flat portion 7'" inclined at the angle θ' is formed on the inner surface of the coil 7 in this manner, the operating wires 8 and 9 slide along the gradient with reduced resistance when they are pulled to the proximal end side. When the wires 8 and 9 are pushed to the distal end side, on the other hand, they move resisting the gradient. In this case, however, no force is generated to press the wires 8 and 9 against the coil 7, so that the gradient never causes the resistance to increase.

Figure 3:
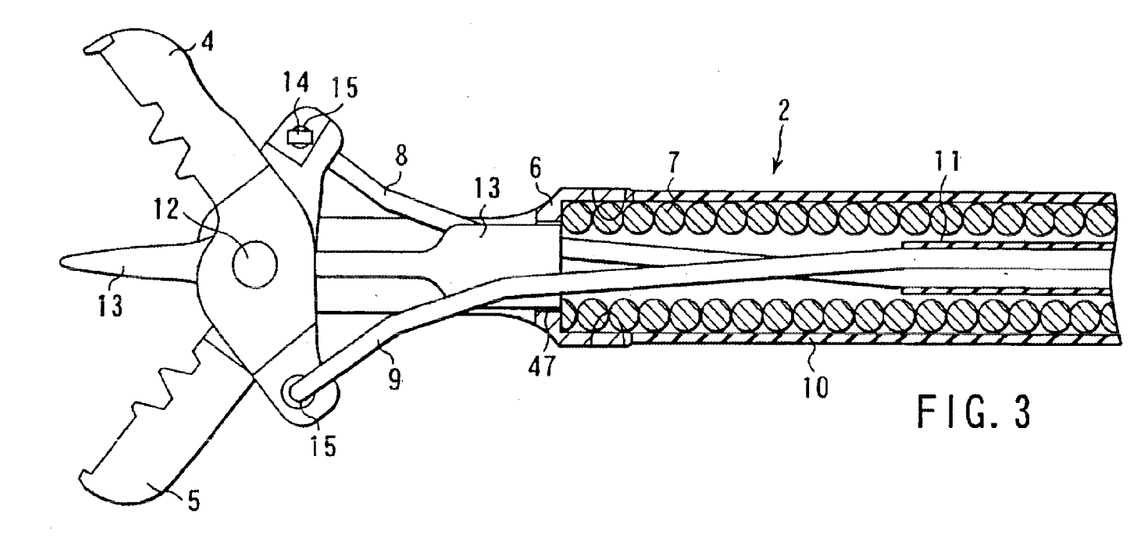
FIG. 3 is a side view, partially in section, showing the biopsy cups of the endoscopic biopsy forceps of FIG. 1 in an open state.

Those portions of the operating wires 8 and 9 which are located in the coil 7 are passed substantially entirely through the inner tube 11. As shown in FIG. 3, they are only passed through the bore of the inner tube 11 without being fixed to the tube 11. Thus, the wires 8 and 9 can move back and forth in the tube 11. Further, the outer surface of the inner tube 11 is embossed to reduce the area of contact between the tube 11 and the coil 7, thereby improving the transmissibility and operating efficiency. It is to be desired, in this case, that the embossed roughness should preferably be adjusted to 200 μm or less, and further preferably to 13 to 20 μm, in terms of the width of irregularities. In order to smoothen the movement of the operating wires 8 and 9, moreover, at least a part of the coil 7, wires 8 and 9, and/or inner tube 11 is coated with silicone oil as lubricant, and the surface roughness of the element wires of the coil is adjusted to 0.8 S (JIS).

Figure 9:
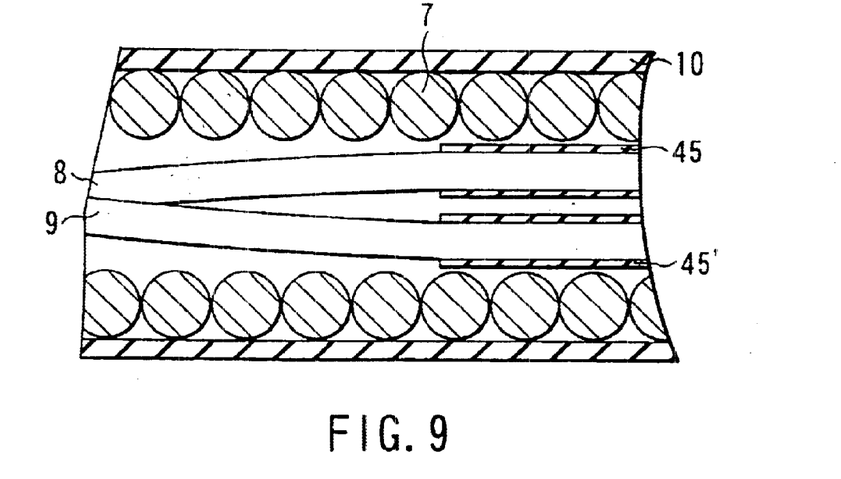
FIG. 9 is an enlarged sectional view showing a modification of an inner tube through which an operating wire is passed.

As shown in FIG. 9, moreover, the inner tube 11 may be formed by coating the respective surfaces of the operating wires 8 and 9 with resin members 45 and 45' by tubing, heat-shrinking, dipping, or spraying, in order to improve the assembly efficiency and lower the parts cost. It is to be understood, in this case, that the tube 11 may be embossed and coated with silicone oil in the same manner as previously.

In order to further improve the capability of the needle 13 to puncture tissue, the thickness of the needle 13 should preferably be adjusted to between 0.02 mm and 0.3 mm, and further preferably to 0.15 mm. The needle 13 may be fabricated by pressing, cold forging, or photo-etching.

Figure 4:
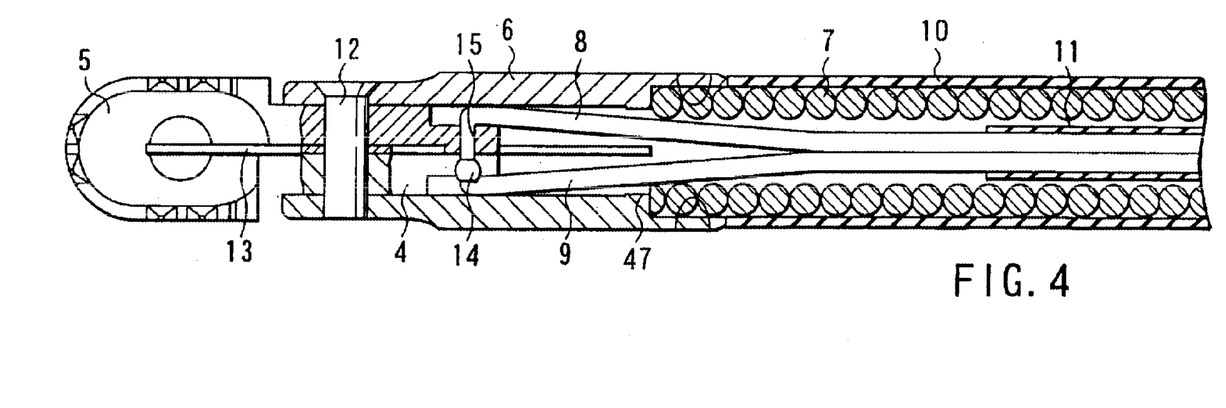
FIG. 4 is a sectional view taken along line 4—4 of FIG. 2A.

As is clearly shown in FIG. 4, the respective distal end portions of the operating wires 8 and 9 are bent once substantially at right angles, and are inserted individually into holes 15 in the respective proximal end side portions of the biopsy cups 4 and 5. In order to prevent the operating wires 8 and 9 from slipping out of the holes 15, the respective distal ends of the wires 8 and 9, bent substantially at right angles, are formed with a stopper portion 14. The stopper portion 14 is crushed under pressure in the axial direction of the wires or perpendicular to their axes. As shown in FIG. 4, one end of the pin 12 is countersunk, and the other end is fixed to the cup holding member 6 by laser welding or caulking.

Figure 10:
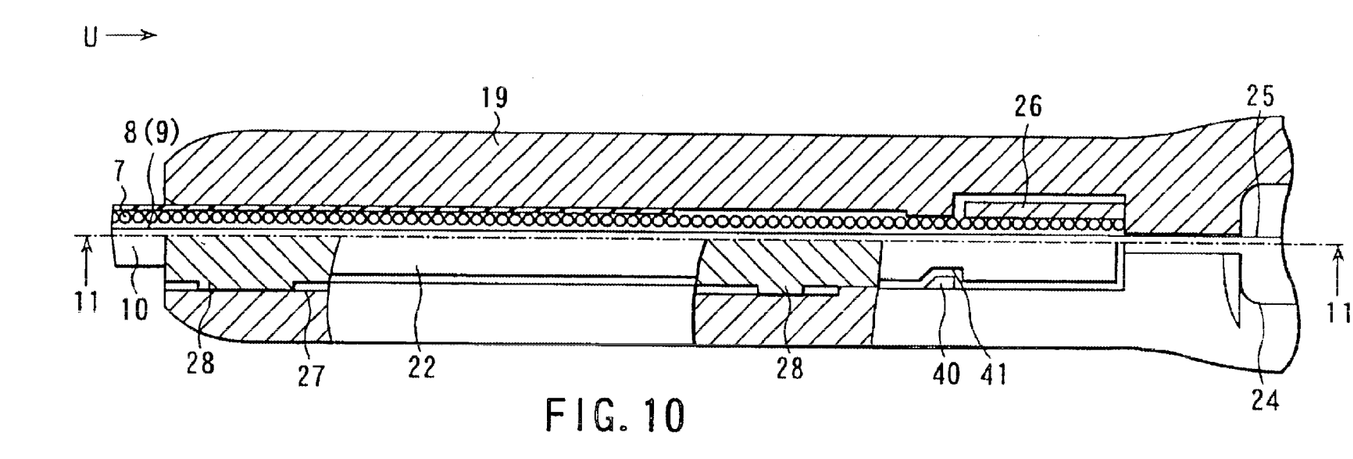
FIG. 10 is a detailed view of a portion indicated by arrow X in FIG. 1, the upper half of which is sectional.
Figure 11:
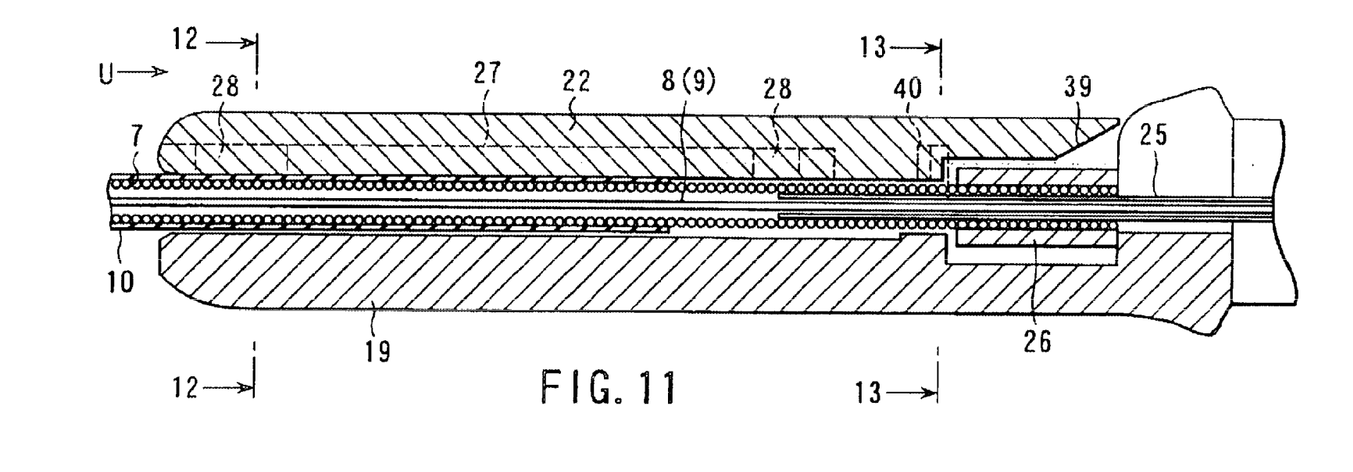
FIG. 11 is a sectional view taken along line 11—11 of FIG. 10.
Figure 12:
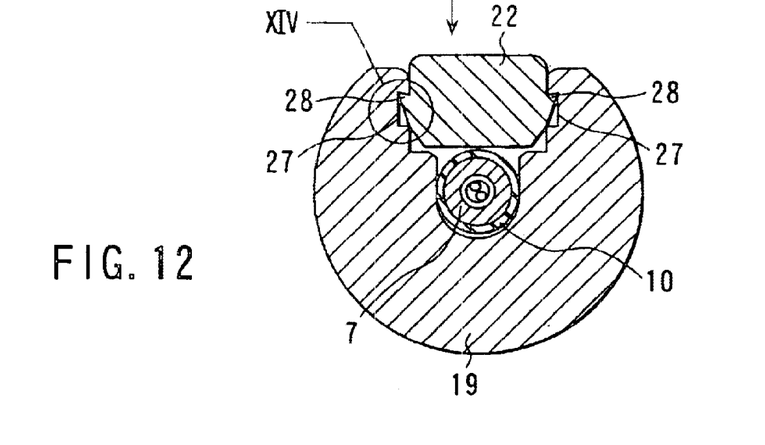
FIG. 12 is a sectional view taken along line 12—12 of FIG. 11.

As shown in FIG. 1, on the other hand, the operating section 3 is composed of an operating section body 19 and a slider 43. As shown in FIGS. 10 and 11, a cylindrical stopper 26 is fixed to the proximal side of the coil 7 by auto-slicing, caulking, brazing, soldering, or ultrasonic welding. The proximal side of the insert section 2 that includes the stopper 26 is located in the operating section body 19, and can be fixed to the body 19 as a body lid 22 is depressed in the direction indicated by arrow T in FIG. 12 so that its click portions 28 are fitted individually in grooves 27 that are formed on the body 19. With this arrangement, the operating section body 19 and the body lid 22 can be assembled with improved efficiency.

Figure 13:
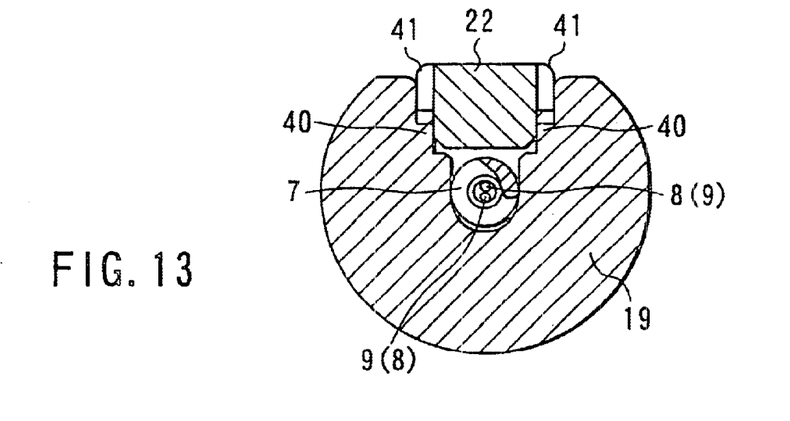
FIG. 13 is a sectional view taken along line 13—13 of FIG. 11.

Further, the body lid 22 may be fixed to the operating section body 19 in a manner such that it is slid in the direction of arrow U in FIGS. 10 and 11 with the click portions 28 guided along the grooves 27. In this case, the body lid 22 can be prevented from being easily disengaged from the body 19 if it is designed so that recesses 41 (see FIG. 13) therein individually engage retaining portions 40 on the body 19 after the retaining portions 40 are cleared by a taper portion 39 of the lid 22.

Figure 14:
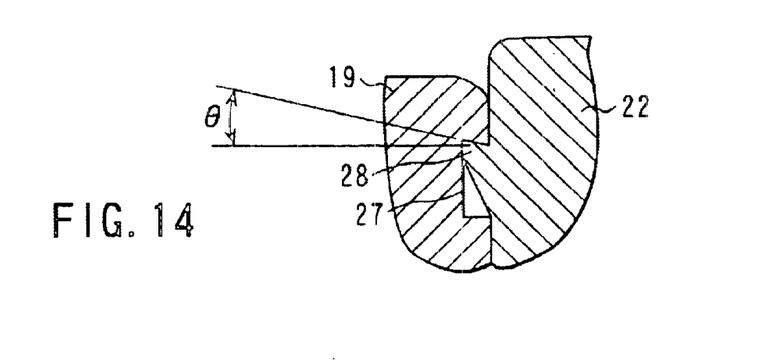
FIG. 14 is an enlarged view of a portion indicated by arrow XIV in FIG. 12.

In order to improve the strength of fixation between the operating section body 19 and the body lid 22, the plane on which the grooves 27 and the click portions 28 engage one another is inclined at $\theta°$ ($0° \leq \theta° < 90°$) lest the lid 22 be easily disengaged from the body 19, as shown in FIG. 14.

Figure 20:
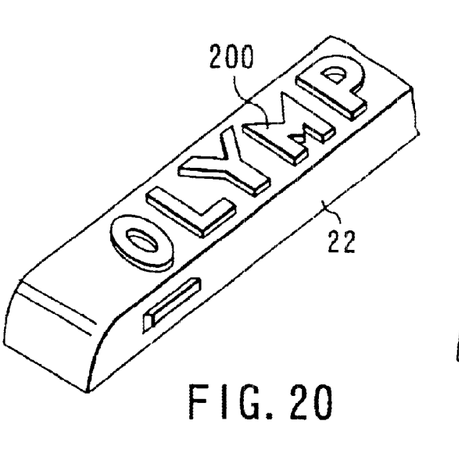
FIG. 20 is a perspective view showing convex characters formed on the outer surface of a body lid of an operating section of the biopsy forceps of FIG. 1.
Figure 21:
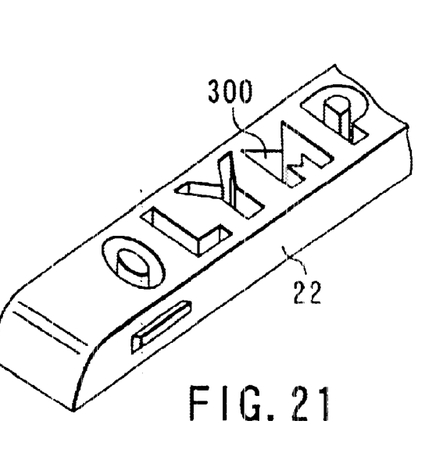
FIG. 21 is a perspective view showing concave characters formed on the outer surface of the body lid of the operating section of the biopsy forceps of FIG.

Further, the body lid 22 may be colored so that it can be identified corresponding to the bore of the forceps channel of the endoscope. As shown in FIG. 20 or 21, moreover, convex characters 200 or concave characters 300 that are indicative of a product name or the like may be put on the outer surface of the lid 22.

Figure 15:
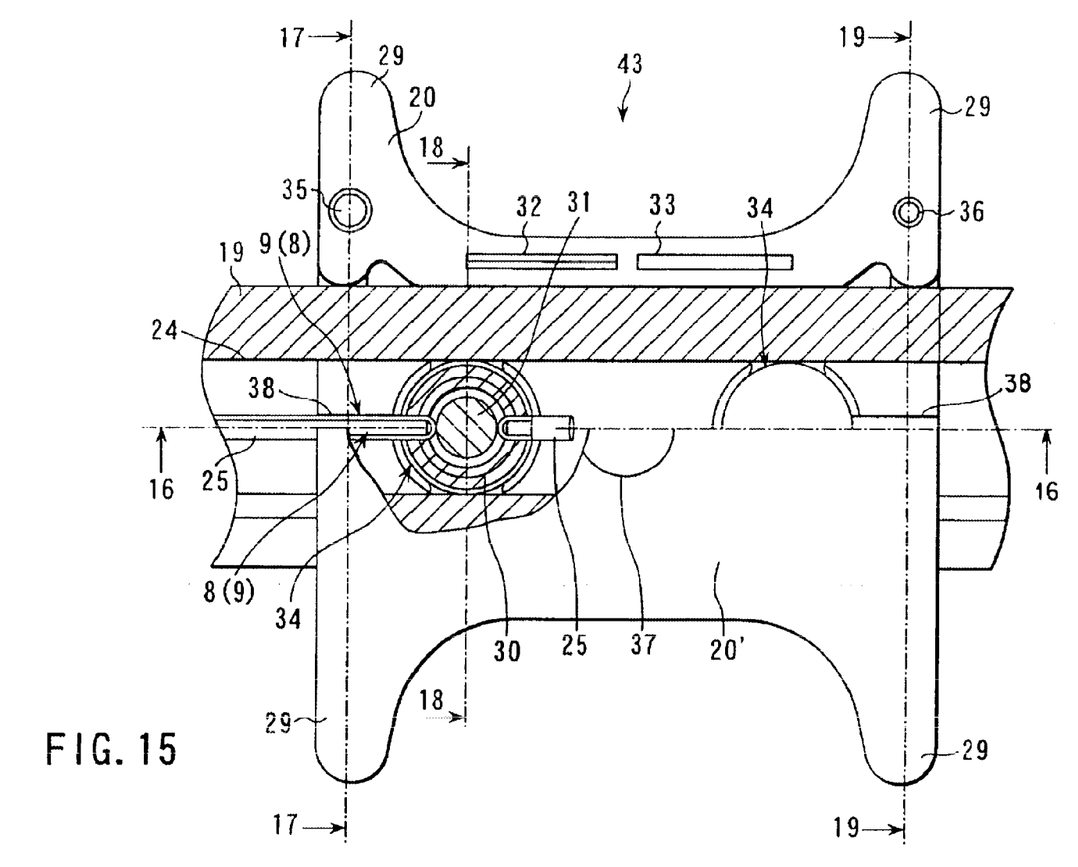
FIG. 15 is a detailed view of a portion indicated by arrow XV in FIG. 1, the upper half of which is sectional.
Figure 16:
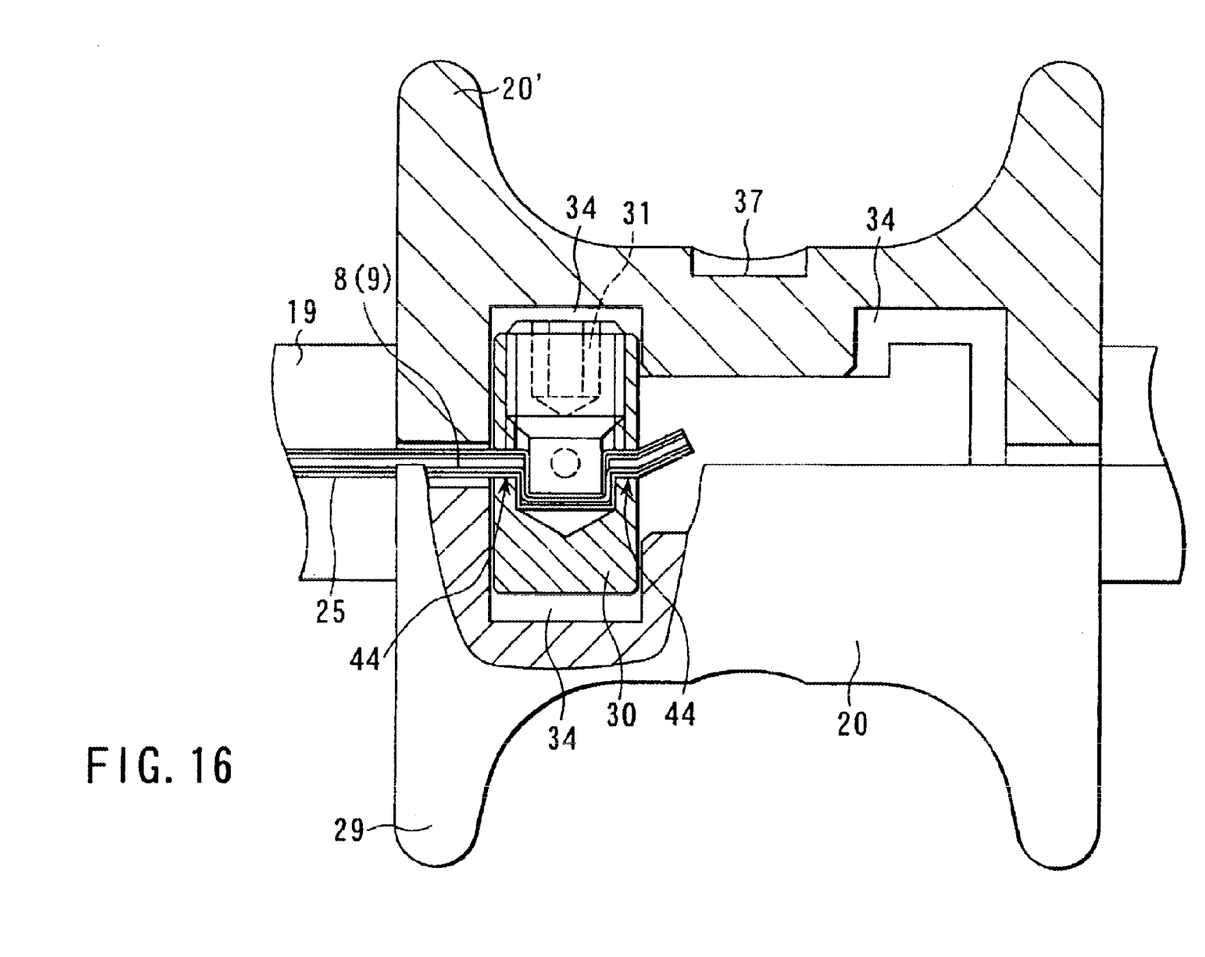
FIG. 16 is a sectional view taken along line 16—16 of FIG. 15.
Figure 17:
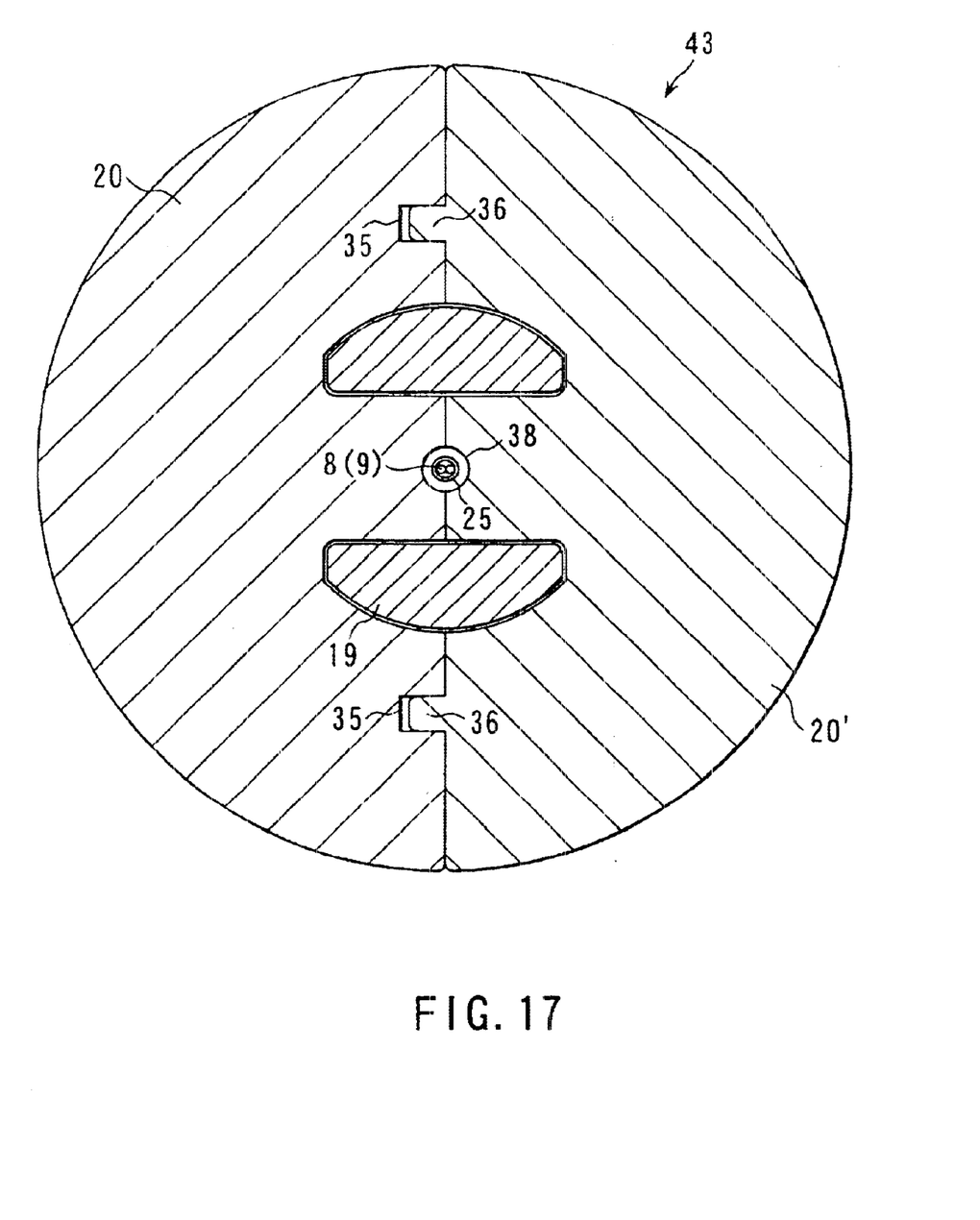
FIG. 17 is a sectional view taken along line 17—17 of FIG. 15.
Figure 18:
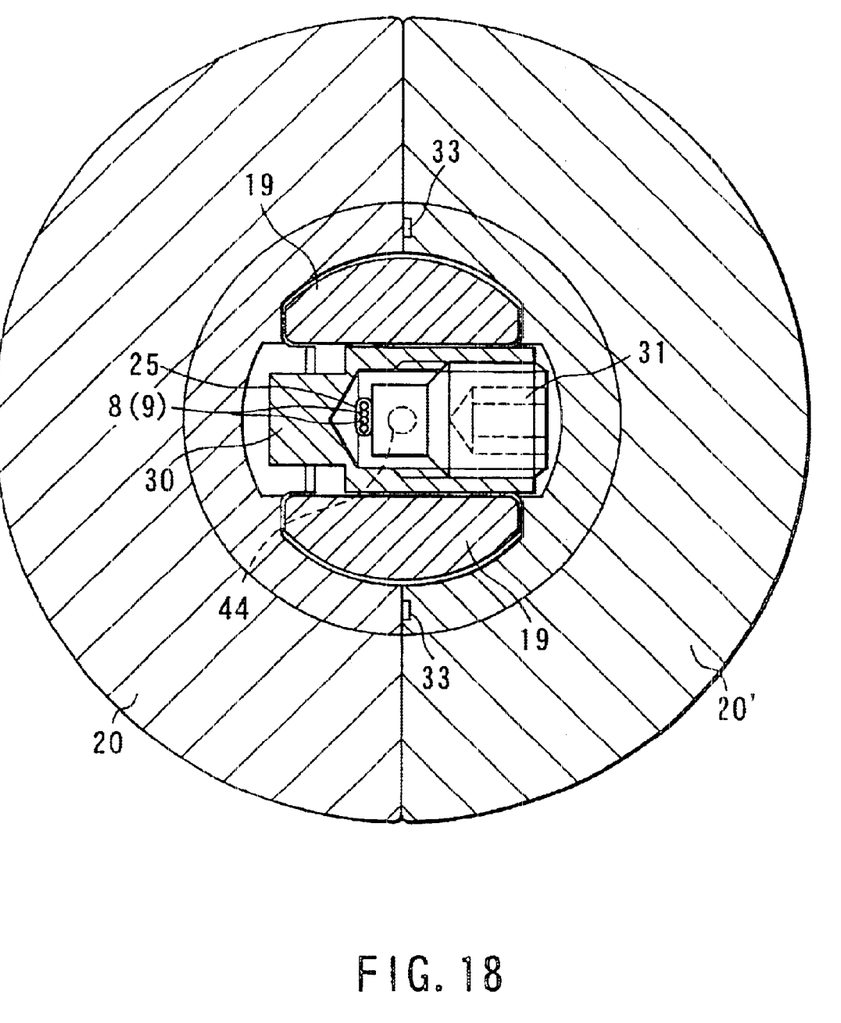
FIG. 18 is a sectional view taken along line 18—18 of FIG. 15.
Figure 19:
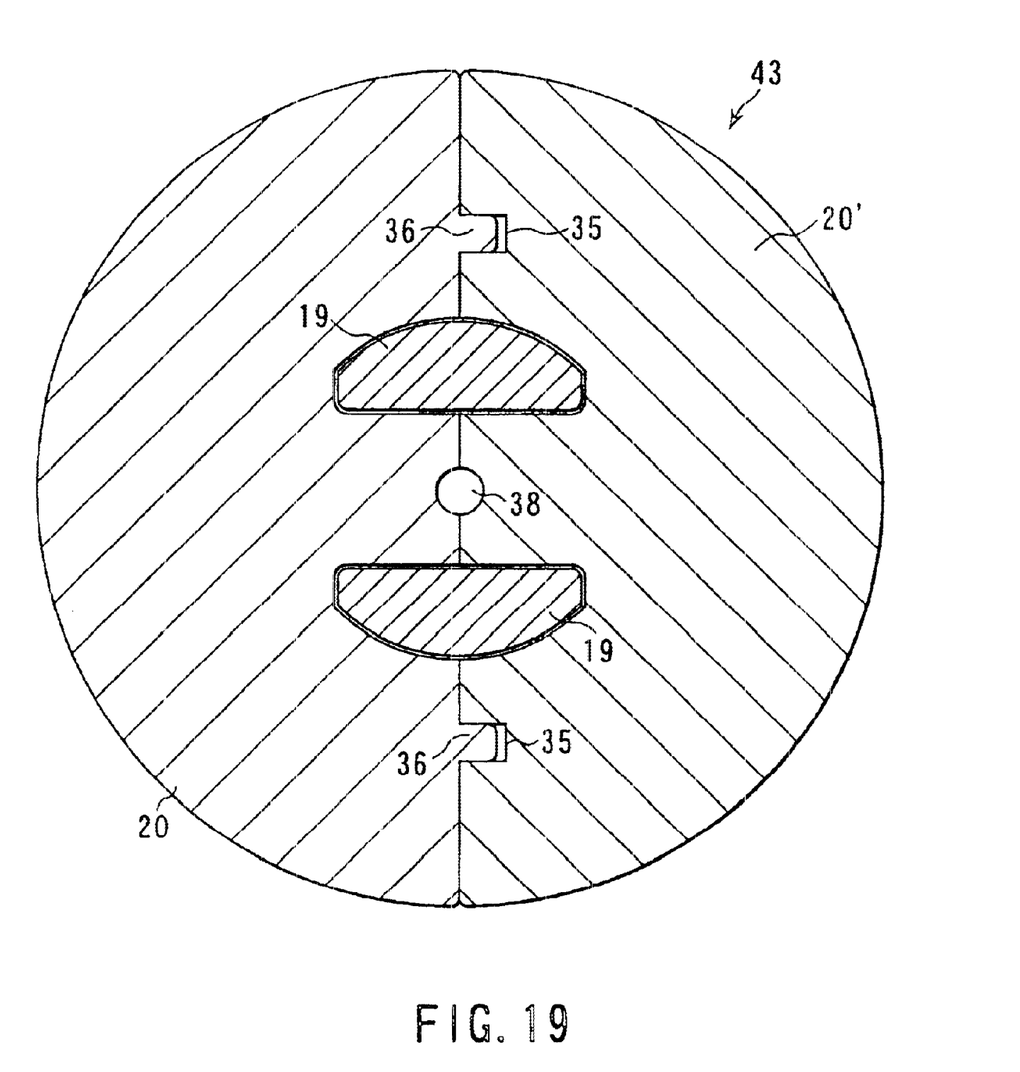
FIG. 19 is a sectional view taken along line 19—19 of FIG. 15.

As shown in FIGS. 15, 16 and 18, the respective proximal end portions of the operating wires 8 and 9 are located in an operating pipe 25 that has a bore. Further, the proximal end portion of the pipe 25 is fitted in a side hole 44 of a stopper 30, and is screwed to the stopper 30 as the pipe 25 including the wires 8 and 9 is deformed by means of a screw 31. Thus, the fixing strength of the wires 8 and 9 is improved. The proximal end portions of the operating wires 8 and 9 including the operating pipe 25, stopper 30, and screw 31 are arranged in a manner such that the stopper 30 engages recesses 34 in slider members 20 and 20' that constitute the slider 43. As shown in FIGS. 15, 17 and 19, moreover, the slider members 20 and 20' are bonded to each other by ultrasonic welding or the like in a manner such that projections 36 of the slider member 20' is individually in engagement with recesses 35 of the slider member 20. In the ultrasonic welding operation, two pairs of symmetrical projections 32 on the slider members 20 and 20' are melted so that the members 20 and 20' are welded to each other. In this case, recesses 33 are escapes that prevent formation of gaps in junctions when the projections 32 are melted. Further, the slider members 20 and 20' are composed of two symmetrical components of the same shape, so that they can be assembled without directivity, and the parts cost can be lowered. An escape 37 is a depression for preventing external projection that is attributable to pin-gate processing.

A stopper 21 (see FIG. 1) functions as a regulating member for the slide of the slider 43 between slits 24 that are formed extending in the longitudinal direction of the operating section body 19. With use of the stopper 21, the operating pipe 25 can be prevented from being disengaged from the coil 7 when the slider 43 is slid at a fixed stroke, and the distance between the slider 43 and a thumb ring 23 on the proximal end of the body 19 can be adjusted to facilitate the operation.

In the present embodiment, the outer tube 10, inner tube 11, and resin members 45 and 45' are formed of the following plastic materials and their combinations. The plastic materials include, for example, polyolefin plastic materials such as high-density polyethylene (HDPE), low-density polyethylene (LDPE), linear low-density polyethylene (LLDPE), polyethylene terephthalate (PET), polypropylene (PP), polybutylene terephthalate (PBT), etc., fluoroplastic materials such as polytetrafluoroethylene (PTFE), tetrafluoroethylene-perfluoro-alkoxy-ethylene resin (PFA), tetrafluoroethylene-hexafluoropropylene resin (FEP), tetrafluoroethylene-ethylene (ETFE), etc., plastic materials such as polyamide (PA), polyacetal (POM), polyether-ether-ketone (PEEK), polycarbonate (PC), acrylonitrile-butadiene-styrene resin (ABS), etc.

Further, the biopsy cups 4 and 5 and the cup holding member 6 are formed of the following metal or plastic materials. The metal materials include, for example, stainless steel, aluminum, nickel, brass, titanium, iron, phosphor bronze, tungsten, gold, silver, copper, $SF_{20}T$ (ferrite-based stainless steel, chemical components: $C \leq 0.05$ wt %, $Si \leq 1$ wt %, $Mn \leq 2$ wt %, $P \leq 0.05$ wt %, $S \geq 0.15$ wt %, $Cr=19$ to 21 wt %, $Mo=1.5$ to 2.5 wt %, $Pb=0.1$ to 0.3 wt %, and $Te=0.01$ to 0.07 wt %), etc. or alloys of these metals. The plastic materials include, for example, polyolefin plastic materials, such as high-density polyethylene (HDPE), low-density polyethylene (LDPE), linear low-density polyethylene (LLDPE), polyethylene terephthalate (PET), polypropylene (PP), polybutylene terephthalate (PBT), etc., fluoroplastic materials, such as polytetrafluoroethylene (PTFE), tetrafluoroethylene-perfluoro-alkoxy-ethylene resin (PFA), tetrafluoroethylene-hexafluoropropylene resin (FEP), tetrafluoroethylene-ethylene (ETFE), etc., polyamide (PA), polyacetal (POM), polyether-ether-ketone (PEEK), polycarbonate (PC), acrylonitrile-butadiene-styrene resin (ABS), liquid crystal polymers, etc.

Furthermore, the coil 7, operating wires 8 and 9, and needle 13 are formed of metal materials, such as stainless steel, aluminum, nickel, brass, titanium, iron, phosphor bronze, tungsten, gold, silver, copper, etc. or alloys of these metals or high-tensile-strength materials (materials having high resistance to tension) based on these metals.

In the arrangement of the present embodiment described above, the operating wires 8 and 9 are slid in the bore of the coil 7 by means of the slider 43 that can slide on the operating section body 19. As this is done, the biopsy cups 4 and 5 that are connected to the respective distal ends of the operating wires 8 and 9 are opened or closed, whereupon tissue in an organism is biopsied by means of the cups 4 and 5. In this case, the micro-flat portion 7', 0.2 to 0.3 mm wide, is formed on the inner surface of the coil 7. If the coil 7 is curved in the manner shown in FIG. 22, therefore, the plastic tube 11 on the respective outer surfaces of the operating wires 8 and 9 can never get into the spaces between the element wires of the coil 7 and hinder the movement of the wires 8 and 9. Thus, the force that is applied to the operating section 3 can be efficiently transmitted to the treatment sections 4 and 5 by means of the wires 8 and 9, respectively, so that a strong force can be generated during treatment.

According to the endoscopic biopsy forceps 1 of the present embodiment, as described above, the force that is applied to the operating section 3 can be efficiently transmitted to the biopsy cups 4 and 5 without being influenced by the curved state of the endoscope, so that tissue can be easily biopsied with a light force. Thus, a doctor or care assistant can be eased of his/her burden during treatment operation. Since the inside diameter of the coil 7 can be made greater than that of a conventional coil, moreover, a generous clearance can be secured between the operating wires 8 and 9, so that the operating efficiency of the wires 8 and 9 can be raised. Furthermore since the forceps 1 requires no substantial change in construction, its function can be improved without entailing any increase in cost.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic instrument comprising:
   a flexible insert section capable of being passed through a forceps channel of an endoscope,
   an opening wire located in a bore of the insert section and movable in the axial direction of the insert section;
   an operating section connected to the proximal end of the insert section and used to move the operating wire forward and backward; and
   a treatment section attached to the distal end of the insert section and adapted to be operated as the operating wire is moved forward and backward,
   wherein the operating wire is composed of at least one wire member, a resin member is located on or adhered to at least a part of the outer surface of the operating wire, at least the inner surface of the insert section is formed of a metallic coil, and a micro-flat portion is provided at least on that surface portion of an element wire of the coil which faces the operating wire to cover substantially an overall length of the coil.

2. An endoscopic instrument according to claim 1, wherein said micro-flat portion is provided only on that surface of the element wire of the coil which faces the operating wire.

3. An endoscopic instrument comprising:
   a flexible insert section capable of being passed through a forceps channel of an endoscope;
   an operating wire located in bore of the insert section and movable in the axial direction of the insert section;
   an operating section connect to the proximal end of the insert section and used to move the operating wire forward an backward; and
   a treatment section attached to the distal end of the insert section and adapted to be operated as the operating wire is move forward and backward,
   wherein the operating wire is composed of at least one wire member, a resin member is located on or adhered to at least a part of the outer surface of the operating wire, at least the inner surface of the insert section is formed of a metallic coil having a circular cross section, and a micro-flat portion is provided only on that surface portion of an element wire of the coil which faces the operating wire.

4. An endoscopic instrument according to claim 1, wherein said micro-flat portion is provided only on that surface portion of the element wire of the coil which faces the operating wire.

5. An endoscopic instrument according to claim 1, wherein said micro-flat portion is inclined at a given angle to the longitudinal central axis of the coil so as to approach the longitudinal central axis of the coil with distance from the distal end side of the coil.

6. An endoscopic instrument according to claim 1, wherein the length of said micro-flat portion for the cross section of each element wire extending in the longitudinal direction of the coil is adjusted to be between 0.02 and 0.3 mm as the coil is viewed along the cross section in the longitudinal direction.

7. An endoscopic instrument according to claim 1, wherein at least a part of the inner surface of said coil, the surface of the resin member of said operating wire, and/or the surface of said operating wire is coated with lubricant.

8. An endoscopic instrument according to claim 7, wherein said lubricant is silicone oil.

9. An endoscopic instrument according to claim 1, wherein the surface roughness of the element wire of said coil is lower than 0.8 S (JIS).

10. An endoscopic instrument according to claim 1, wherein said resin member is closely fixed to the operating wire by extrusion molding, heat-shrinking, dipping, or spraying.

11. An endoscopic instrument according to claim 10, wherein the outer surface of said resin member is embossed with an irregularity width of 200 $\mu$m or less.

12. An endoscopic instrument according to claim 1, wherein said resin member is a tubular molding to be moved forward and backward on the outer periphery of the operating wire.

13. An endoscopic instrument according to claim 12, wherein the outer surface of said resin member is embossed with an irregularity width of 200 $\mu$m or less.

14. An endoscopic instrument according to claim 1, wherein said coil and said operating wire are formed of metallic wires of stainless steel, aluminum, nickel, brass, titanium, iron, phosphor bronze, tungsten, gold, silver, copper, or alloys of said metals.

15. An endoscopic instrument according to claim 1, wherein said operating wire is a solid wire.

16. An endoscopic instrument according to claim 1, wherein said operating wire is a stranded wire.

17. An endoscopic instrument according to claim 1, wherein said operating wire is formed of high-tensile-strength material.

18. An endoscopic instrument according to claim 1, wherein said resin member is formed of a polyolefin plastic material selected from a group consisting of high-density polyethylene (HDPE), low-density polyethylene (LDPE), linear low-density polyethylene (LLDPE), polyethylene terephthalate (PET), polypropylene (PP), or polybutylene terephthalate (PBT), a fluoroplastic material such as polytetrafluoroethylene (PTFE), tetrafluoroethylene-perfluoro-alkoxy-ethylene resin (PFA), tetrafluoroethylene-hexafluoropropylene resin FEP), or tetrafluoroethylene-ethylene (ETFE), a plastic material such as polyamide (PA), polyacetal (POM), polyether-ether-ketone (PEEK), polycarbonate (PC), or acrylonitrile-butadiene-styrene resin (ABS), or a mixture of said materials.

19. An endoscopic instrument according to claim 1, wherein the outer surface of said coil is coated with a polyolefin plastic material selected from a group consisting of high-density polyethylene (HDPE), low-density polyethylene (LDPE), linear low-density polyethylene (LLDPE), polyethylene terephthalate (PET), polypropylene (PP), or polybutylene terephthalate (PBT), a fluoroplastic material such as polytetrafluoroethylene (PTFE), tetrafluoroethylene-perfluoro-alkoxy-ethylene resin (PFA), tetrafluoroethylene-hexafluoropropylene resin (FEP), or tetrafluoroethylene-ethylene (ETFE), a plastic material such as polyamide (PA), polyacetal (POM), polyether-ether-ketone (PEEK), polycarbonate (PC), or acrylonitrile-butadiene-styrene resin (ABS), or a mixture of said materials.

* * * * *